United States Patent
Stones

(10) Patent No.: US 9,027,259 B2
(45) Date of Patent: May 12, 2015

(54) APPARATUS AND METHOD FOR IMPROVED RECOVERY OF LATENT FINGERPRINTS

(76) Inventor: William Bryon Stones, Queen Creek, AZ (US)

(*) Notice: Subject to any disclaimer, the term of this patent is extended or adjusted under 35 U.S.C. 154(b) by 0 days.

(21) Appl. No.: 13/309,934

(22) Filed: Dec. 2, 2011

(65) Prior Publication Data

US 2012/0141669 A1    Jun. 7, 2012

Related U.S. Application Data

(60) Provisional application No. 61/419,189, filed on Dec. 2, 2010.

(51) Int. Cl.
| | |
|---|---|
| *F26B 13/10* | (2006.01) |
| *F26B 21/00* | (2006.01) |
| *B41K 1/00* | (2006.01) |
| *A61B 5/117* | (2006.01) |
| *G06K 9/00* | (2006.01) |

(52) U.S. Cl.
CPC ............... *A61B 5/1172* (2013.01); *G06K 9/00* (2013.01)

(58) Field of Classification Search
CPC ... A61B 5/1172; G06K 9/00; G06K 9/00006; G06K 9/00013
USPC ............ 34/523; 118/31.5, 715, 728, 729, 731
See application file for complete search history.

(56) References Cited

U.S. PATENT DOCUMENTS

| | | | | |
|---|---|---|---|---|
| 5,465,765 | A * | 11/1995 | Martindale | 141/65 |
| 8,272,343 | B1 * | 9/2012 | Weaver et al. | 118/31.5 |
| 2010/0021023 | A1 * | 1/2010 | Lewis et al. | 382/124 |

OTHER PUBLICATIONS

Dadmun, Mark D. Cultivating Methods to Enhance the Quality of Ages Fingerprints developed by Cyanoacrylate Fuming, US. Department of Justice, Document No. 230161, Nov. 2009, 29 pages.*
Stones, W. Bryon, Convak LLC, http://www.convak.com/#!, accessed Oct. 30, 2013.*
Stones, William et al., Convac LLC, https://gust.com/c/convac_llc, accessed Oct. 30, 2013.*

* cited by examiner

*Primary Examiner* — Kelly M Gambetta
(74) *Attorney, Agent, or Firm* — Keith L. Jenkins, Registered Patent Attorney, LLC; Keith L. Jenkins

(57) ABSTRACT

Hydrating an object bearing a latent fingerprint and then selectively drying the object leaving the fingerprint hydrated. The hydrated fingerprint is then coated with cyanoacrylate ester, preferably in a heat accelerated cyanoacrylate ester vacuum chamber. Hydrating is preferably accomplished by chilling the object below a dew point and then exposing the object to humidified air to condense a thin uniform layer of water over the object and latent fingerprint. Drying is preferably done with a vacuum. After drying reaches the preferred state, the CE is heated and coats the condensation-hydrated latent fingerprint. Preferably, the method is implemented in an automated system using one computer-controlled chamber for chilling, condensing, vacuum drying, and CE coating the latent fingerprint. The operator simply puts the object in the chamber, initiates the process by computer, and is prompted by the computer to remove the recovered latent print. Prints unrecoverable by prior art means are recovered.

15 Claims, 4 Drawing Sheets

APPARATUS AND METHOD FOR IMPROVED RECOVERY OF LATENT FINGERPRINTS

RELATIONSHIP TO OTHER APPLICATIONS

This application claims the benefit of U.S. provisional patent application 61/419,189 filed Dec. 2, 2010 for the same inventor.

FIELD OF THE INVENTION

This invention relates to an apparatus and method for improved recovery of latent fingerprints on nonporous surfaces for recovering fingerprints that cannot be recovered by prior art methods and apparatus. The invention further relates to an apparatus and method for improved recovery of latent fingerprints on nonporous surfaces for rehydrating latent fingerprints using an automatic control system with the apparatus.

BACKGROUND

Numerous methods of latent recovery have been developed and implemented resulting in cases being solved that would have been passed over in days past. The Cyanoacrylate Ester (CE) fuming process was developed in the late 1970's and is the most common method of processing currently in use for non-porous materials. Atmosphere CE is a method used to coat latent fingerprint residues with cyanoacrylate ester residue. The process involves an item being enclosed in a chamber, along with a heat source and a humidity source. The heat source is usually a coffee warmer and the humidity source warm water. The water can be introduced with a humidifier or just by placing a jar of warm water into the chamber. The liquid CE is placed into an aluminum weighing tray and heated changing the state from a liquid to a fume. The fume fills the chamber and deposits a white residue on waters and oils on the item. The resulting residue can be dusted with powders, dye stained, or photographed and is permanent until cleaned with acetone.

In the 1980's, CE fuming using Vacuum in a chamber held some promise in the recovery of latent fingerprints on non-porous surfaces. The resulting prints were slight and needed to be dye stained. Advancement to the Vacuum CE fuming technique was introduced in 1989 with the addition of a heating element inside the vacuum chamber enhancing the polymerization of the cyanoacrylate ester (also known as "super glue"), changing the amount of residue on a latent fingerprint and shortening the time needed for processing. Vacuum CE w/HA differs from Vacuum CE in that the CE is vaporized in a quick efficient fashion, similar to the atmosphere process using a hot plate. This allows for a denser concentration of CE particles to be dispersed within the chamber. Since vacuum CE is evenly dispersed in the chamber, increasing the density and number of CE particles results in a thicker deposition of CE on the ridges and no deposit in the valleys. The fact that no deposition occurs in the valleys is common to all vacuum methods. Also common to all vacuum methods is the ability to reprocess an item multiple times. The exception for vacuum CE w/HA when compared to vacuum CE without HA, is that the deposition of CE is much thicker when heated, resulting in having fewer times of processing for a quality latent print.

The history of vacuum cyanoacrylate latent processing is fairly new. It was invented in the 1980's in Canada and spread quickly throughout the forensic community. The chamber consisted of a thick wall PVC pipe with an average inner diameter of about 12-24 inches. An end cap built for the pipe was affixed permanently and an air tight lid was manufactured for the front of the chamber. A valve system was introduced to allow air to be removed from the chamber and sealed to create a vacuum. Items were placed into the chamber for processing along with a tray of liquid cyanoacrylate (CE). Once the chamber was pumped to a complete vacuum, the CE then would boil at room temperature and evaporate into the chamber. The vacuum would then distribute evenly placed spherical molecules of CE throughout the chamber. The molecules would be able to penetrate areas that CE fumes in atmosphere could not. For example, a plastic baggie in an atmosphere chamber would only deposit CE residue on the outer portions of the bag, a vacuum chamber would deposit CE residue on all surfaces of the bag both inner and outer, even if the bag was folded. The resulting print was very light and often powder would not adhere to it, requiring a dye stain to be used. An interesting result was that a latent print recovered using the vacuum CE method could be reprocessed as many times as necessary to build a success latent fingerprint. Since the amount of residue was so light, this method became impractical for everyday use on casework due to the man hours needed. For this reason vacuum CE began to lose favor with latent fingerprint recovery professionals.

In 1989, the present inventor began to experiment with vacuum CE and found the same lackluster results. The present inventor used a desiccator and a small vacuum pump and tried various methods to introduce the CE into the chamber with failed results. That year, the present inventor attended a demonstration of a Vacuum Metal Deposition (VMD) machine and realized that heating elements inside the vacuum chamber were the answer and set about to build a chamber. The present inventor bought a rotary vacuum pump with a 3.5 CFM rating, a three-foot section of sewer pipe with an inner diameter of twelve inches, and an end cap. The end cap was secured to the pipe with epoxy and checked for a good seat. A one-inch thick acrylic lid was machined to fit the front of the pipe with a perfect fit, along with a rubber gasket to create an airtight seal. The lid had a lip cut so as to fit about ⅜ inch into the tank with the remaining on the exterior of the pipe lip. Gas valves and threaded pipe were configured into a three valve inline system so as to allow vacation of atmosphere from the chamber, diversion of suction so the pump can be shut off properly, and the reentry of atmosphere into the chamber through one threaded and sealed port on the rear end cap. A second threaded and sealed port accommodated the vacuum gauge. Two small holes just large enough for wire to be put into the chamber were drilled and a 110 volt extension plug was placed in the interior of the chamber. Those holes were sealed using epoxy and the chamber was ready for testing. Even though the wall thickness was ½ inch, the present inventor was warned to watch for an implosion of the chamber. The present inventor tested the chamber in 1989 with successful results: the chamber held a vacuum for over 6 hours. The present inventor further tested the electricity inside the chamber with a radio. As the atmosphere in the chamber was being pumped down you could hear the radio in the chamber, you could hear the sound from the radio dissipate as sound conducting air was removed from the chamber, and become inaudible indicating that a full vacuum was achieved.

The present inventor tested the heated CE vacuum chamber for latent processing. The first step for the test was to put glass slides in the heated CE vacuum chamber after depositing latent fingerprints on them. The test used a coffee warmer, such as those used with atmosphere-filled latent fingerprint tanks, inside the chamber to heat the CE in the chamber. The next step was to put an aluminum tray on the warmer with about a 1"-1.5" diameter puddle of liquid CE in the tray. The heated CE vacuum chamber was pumped free of atmosphere and power was provided to the warmer. The process was repeated at varying the times, CE amounts, and pressures. The best results for processing were about forty minutes, with about a 1"-1.5" diameter puddle of CE, and a vacuum of twenty-seven inches.

The present inventor's findings were presented, along with the heated CE vacuum chamber, at a Northern California Laser Users Group in 1989. The heated CE vacuum chamber and the process received great interest from colleagues, other agencies and even the Home Office in England. A physics professor in Texas had concerns of the effect of CE fumes on PVC and stated emphatically that an implosion would occur using this type of device. He never saw the heated CE vacuum chamber, nor contacted the present inventor in any way. He was referring to schedule 40 PVC, used for sprinkler systems, which has a very thin wall and wouldn't even hold a vacuum if it could be made large enough. Sewer pipe is made to withstand great pressures, and consequently great vacuum.

Interest dropped off about the process after that, but the present inventor continued to use it for case work. The present inventor used the heated CE vacuum chamber in the Fresno County Sheriff's Department for 2½ years from 1989 to 1992 and at the Northern Utah State Crime Laboratory for three years from 1992 to 1995. Currently the present inventor teaches forensics at the associate degree level and uses the heated CE vacuum chamber in classroom training. The heated CE vacuum chamber has never been cleaned, except for the acrylic lid, and the only mark of sustained use is a crust over the warmer.

The heated CE vacuum chamber was used on one case in Utah in 1995, where a wax cookie box, "Chips Ahoy", had been torn in two for use as a target at a homicide scene. The box was collected and evaluated for processing. The cardboard on the interior would be suitable for ninhydrin (a dye), except this process would destroy latent prints on the waxy coating. It was decided process the waxy coating first with vacuum CE with heat acceleration (HA). After the first process, the item was dusted with a yellow fluorescent powder and viewed with an Omichrome 1000 Å alternate light source. The process began to show ridge detail and needed to be reprocessed. The item was then reprocessed five more times with increasing detail alter each process. The result was two identified latent fingerprints to two suspects, with arrests and convictions in both individuals.

A few companies, Payton Scientific and Coleman for example, are starting to offer vacuum CE with HA, but they are very expensive and out of the buying ability of most law enforcement agencies. The Coleman unit retails for around $2,000 and the Peyton Scientific unit for about $35,000. The American Society of Crime Laboratory Directors (ASCLD) does not currently recognize vacuum CE with HA, and it will take extensive testing and review procedures to secure certification for any agency to use it.

The atmosphere CE method is in common use for most law enforcement agencies and laboratories. The method involves placing items in an enclosed chamber at one atmosphere and then introducing humidity and CE fumes. The humidity can be introduced as easily as placing warm water into the chamber, or by using a hygrometer and humidifier. The ideal is usually between 70-80% humidity inside the chamber. Too much humidity will cause the CE fumes to stick to the water vapor in the chamber, coating over items and resulting in a white residue over the entire item. Too little humidity will result in a poor quality latent print. CE fumes can be introduced by chemical or heating methods. Chemical methods rely on a chemical action when drops of CE are placed in contact with treated cotton. Heating methods use one of two common heat sources, a coffee warmer (125 degrees) and a hot plate (400-500 degrees). The (preferred method of contact with the heat is an aluminum weighing tray, with liquid CE in direct contact with the heat source. With a coffee warmer, the CE fumes are heated at a slow rate and often an observer can see a light plume of white smoke rising from the dish. Depending on the size of the tank, it can take as little as fifteen minutes to process an item. Using a hot plate polymerizes the CE in a different manner. The CE will heat rapidly and a large cloud of smoke will fill the chamber quickly. This produces a thicker residue height on the ridges and has increased performance in regard to older fingerprints. This method is preferable when you have a very large tank or makeshift chamber.

The drawback of both methods is that humidity is required for both. When humidity fills the chamber and deposits on the item, it deposits on both the ridge and the valley of a latent fingerprint. Most latent prints recovered are composed of sebaceous fluids and less of water content. When humidity is applied, moisture does deposit on the sebaceous ridge detail and enhance the latent print. Humidity, while enhancing a latent ridge detail, also coats the valley, preventing the latent from being processed any subsequent times. If it is processed a second time, the latent print coats white and all ridge detail is lost.

Older latent fingerprints have traditionally not even been processed when the age of the latent fingerprint that has been exposed to a hot environment (i.e. Arizona summer heat) was discovered to be four days or more. It was deemed useless and a waste of time to go through latent processing when the result will be negative. Light latent fingerprints are subject to a similar decision making process. When a light latent fingerprint is discovered, additional processing using atmosphere CE is not possible. Therefore, the only option is to dye stain the CE ridge and hope enough dye is present to be visible using an Alternate Light Source, (ALS). An alternative to this problem is to process the item with vacuum CE w/HA. Light latent fingerprints using this method of processing can be reprocessed many times to enhance CE ridge height. Often even vacuum CE w/HA will not have a successful result on older latent fingerprints.

Normal humidity processes will not work with the vacuum CE w/HA process. You cannot introduce hot water in a vacuum: water needs air to bond to distribute throughout the chamber.

Humidity appears to be the culprit in atmosphere CE processing. When atmosphere CE is done without humidity the results are poor but in some cases, able to be reprocessed. This does not however, give an adequate result on a sustainable basis. Vacuum CE does have the ability to reprocess, but does not leave enough ridge height to accommodate powder dusting. Vacuum CE with heat acceleration (HA) does give the proper ridge height for powder dusting and is able to be reprocessed. In some cases, however, older prints may not be recoverable by just using this method or any other in current use.

Therefore, a need exists for an apparatus and method for improved recovery of latent fingerprints on nonporous surfaces that can recover latent fingerprints that cannot be recovered by prior art means. A need also exists for an apparatus and method for improved recovery of latent fingerprints on nonporous surfaces that can rehydrate latent fingerprints for a vacuum CE with H/A process. A need also exists for an apparatus and method for improved recovery of latent fingerprints on nonporous surfaces that uses an automatic controller and can be automated to reduce the man-hours needed.

OBJECTS AND FEATURES OF THE INVENTION

A primary object and feature of the present invention is to overcome the above-mentioned problems and fulfill the above-mentioned needs.

Another object and feature of the present invention is to provide an apparatus and method for improved recovery of latent fingerprints on nonporous surfaces that can recover latent fingerprints that cannot be recovered by prior art means. Another object and feature of the present invention is to provide an apparatus and method for improved recovery of latent fingerprints on nonporous surfaces that hydrates latent fingerprints for a vacuum CE with H/A process. Another object and feature of the present invention is to provide an apparatus and method for improved recovery of latent fingerprints on nonporous surfaces that uses an automatic controller. Another object and feature of the present invention is to provide an apparatus and method for improved recovery of latent fingerprints on nonporous surfaces that is marketable and operates as a single unit, in which the user simply places an object suspected of having latent fingerprints into the chamber, and all operations take place in a single chamber under computerized control.

It is an additional primary object and feature of the present invention to provide an apparatus and method for improved recovery of latent fingerprints on nonporous surfaces that is safe, inexpensive, easy to clean, and handy. Other objects and features of this invention will become apparent with reference to the following descriptions.

SUMMARY OF THE INVENTION

In accordance with a preferred embodiment hereof, the present invention provides an apparatus and method for improved recovery of latent fingerprints on nonporous surfaces that can recover latent fingerprints that cannot be recovered by prior art means. The object that bears the fingerprint is first chilled and then exposed to atmospheric humidity to condense water onto the object and the fingerprint. The object, with condensation, is placed the heated CE vacuum chamber and the chamber is pumped down towards vacuum as the CE is heated. Based on the present inventor's discovery that, during exposure to vacuum, the condensation sticks longer to the sebaceous fluid which forms the finger print than to the object upon which the fingerprint rests, the CE heater is controlled to release CE vapors at a time when the condensation is still sticking to the sebaceous fluid but has evaporated from the object. The combination of moisture and sebaceous fluid retains the CE, providing recovery of fingerprints that would otherwise not be recoverable.

The controller employs a laptop computer with a USB control board for operation of the vacuum pump and heater with monitoring of the time, internal chamber pressure, and heater temperature. Software on the laptop calculates the time to turn on the CE heater based on chamber pressure and signals the USB controller to turn on the CE heater. The controller also determines the time at which the process is complete and re-pressurizes the chamber. The software may include a database of appropriate times for CE vapor deposition as a function of the material on which the fingerprint resides. That is, some materials may release condensation faster or slower than other materials, making the preferred timing for CE vapor deposition different for each material.

The chamber pressure transducer may be a relative pressure transducer, requiring correction for altitude.

The invention provide an apparatus for recovering a latent fingerprint that is on an object, the apparatus including: means for providing a thin uniform coating of water over the object bearing the latent fingerprint and over the latent fingerprint; and means for exposing the object bearing the latent fingerprint to a vacuum for a period of time sufficient to remove the thin uniform coating of water from the object and not entirely remove the water from the fingerprint. The apparatus, where the means for providing a thin uniform coating of water includes: means for chilling the object bearing the latent fingerprint to a temperature below the dew point of a particular supply of humidified air; and means for exposing the object bearing the latent fingerprint to humidified air from the particular supply of humidified air for a period of time sufficient to condense water from the humidified air onto the object bearing the latent fingerprint and onto the latent fingerprint. The apparatus, where the means for chilling includes a cold chamber able to contain either a cold gas or a combination of cold gases. The apparatus, where the means for exposing the object bearing the latent fingerprint to humidified air includes a wet chamber configured to contain humidified air. The apparatus, where the means for exposing the object bearing the latent fingerprint to a vacuum includes a heat accelerated cyanoacrylate ester vacuum chamber. The apparatus, where the cold chamber, the wet chamber, and the heat accelerated cyanoacrylate ester vacuum chamber comprise a single chamber. The apparatus, further including means for exposing the condensation-hydrated fingerprint to cyanoacrylate ester for a period of time sufficient to coat the condensation-hydrated latent fingerprint with the cyanoacrylate ester. The apparatus, where the means for exposing the condensation-hydrated latent fingerprint to cyanoacrylate ester includes a heat accelerated cyanoacrylate ester vacuum chamber. The apparatus, where the heat accelerated cyanoacrylate ester vacuum chamber further includes an insulating pad able to insulate the object from an interior surface of the heat accelerated cyanoacrylate ester vacuum chamber. The apparatus, further including a single hermetically resealable heat accelerated cyanoacrylate ester vacuum chamber for receiving the object bearing the latent fingerprint, where the single hermetically resealable heat accelerated cyanoacrylate ester vacuum chamber includes: the means for providing a thin uniform coating of water over the object bearing the latent fingerprint, where the means for providing a thin uniform coating of water includes: means for chilling the object bearing the latent fingerprint to a temperature below the dew point of a supply of humidified air; and means for exposing the object bearing the latent fingerprint to humidified air from the supply of humidified air for a period of time sufficient to condense water from the humidified air onto the object bearing the latent fingerprint; the means for exposing the object bearing the condensation-hydrated latent fingerprint to a vacuum for a period of time sufficient to remove the thin uniform coating of water from the object and not entirely remove the water from the latent fingerprint. The apparatus, where the single hermetically resealable heat accelerated Cyanoacrylate Ester vacuum chamber further includes means for exposing the condensation-hydrated fingerprint to cyanoacrylate ester for a period of time sufficient to coat the condensation-hydrated fingerprint with the cyanoacrylate ester. The apparatus, further including a controller coupled to the single hermetically resealable heat accelerated cyanoacrylate ester vacuum chamber and able to control the chilling means, the supply of humidified air, the vacuum means, and the cyanoacrylate ester means, all in timing relationships that enable recovering a latent fingerprint without operator intervention. The apparatus, where the controller includes a USB control board communicatively coupled to a computer, where the computer includes control software for the apparatus. The apparatus, further including at least one computer-controllable valve for controlling one of a cold gas supply, a vacuum source, and a humidified air supply. The apparatus, further including at least one computer-readable sensor to sense at least one of chamber temperature, a chamber pressure, cyanoacrylate ester heater temperature, an object temperature, a condensation state, a power ON/OFF state, and at least one valve state.

The invention further provides a method of using the apparatus including the steps of: sealing the object bearing the latent fingerprint in the single hermetically resealable heat accelerated cyanoacrylate ester vacuum chamber; initiating the control software to initiate recovering the latent fingerprint; responsive to a prompt from the computer, removing the object bearing a recovered latent fingerprint from the hermetically resealable heat accelerated cyanoacrylate ester vacuum chamber.

The invention further provide a method of recovering a latent fingerprint that is on an object, the method including the steps of: providing a thin uniform coating of water over the object bearing the latent fingerprint; and exposing the object bearing the latent fingerprint to a drying influence for a period of time sufficient to remove the thin uniform coating of water from the object and not entirely remove the water from the fingerprint. The method, where the step of providing a thin uniform coating of water includes the steps of: chilling the object bearing the latent fingerprint to a temperature below the dew point of a supply of humidified air; and exposing the object bearing the latent fingerprint to humidified air from the supply of humidified air for a period of time sufficient to condense water from the humidified air onto the object bearing the latent fingerprint. The method, further including the step of exposing the hydrated fingerprint to cyanoacrylate ester for a period of time sufficient to coat the hydrated fingerprint with the cyanoacrylate ester. The method, where the drying influence is a vacuum.

BRIEF DESCRIPTION OF THE DRAWINGS

The above and other objects and advantages of the present invention will become more apparent from the following description taken in conjunction with the following drawings in which.

DETAILED DESCRIPTION OVINE REST MODES AND PREFERRED EMBODIMENTS OF THE INVENTION

Figure 1:
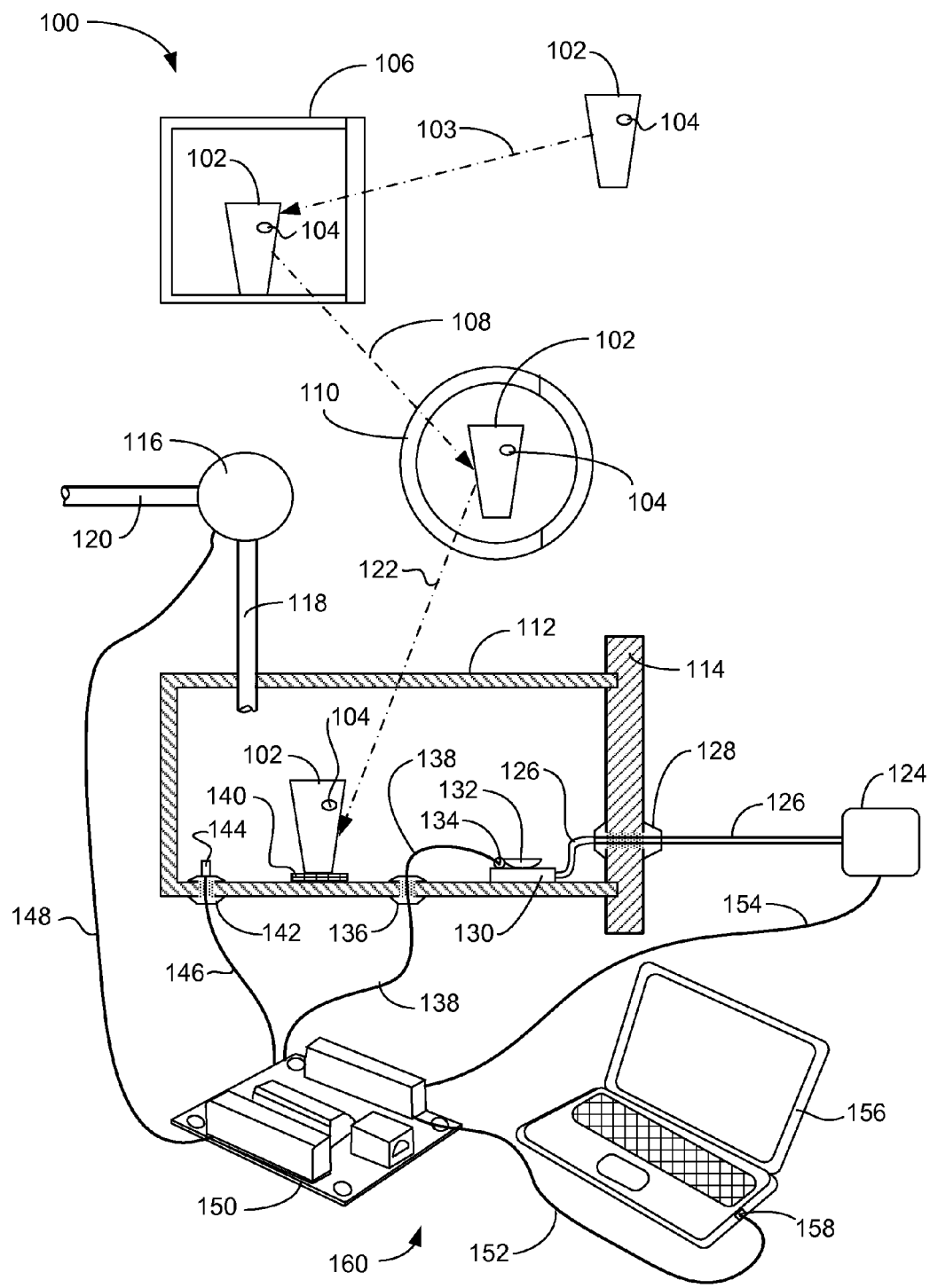
FIG. 1 is a diagram illustrating an exemplary apparatus for improved recovery of latent fingerprints on nonporous surfaces, according to a preferred embodiment of the present invention.

FIG. 1 is a diagram illustrating an exemplary apparatus 100 for improved recovery of latent fingerprints on nonporous surfaces, according to a preferred embodiment of the present invention. An object 102 (exemplified here as a drinking glass) having at least a portion of non-porous surface that may bear a latent fingerprint 104 may be acquired from a crime scene or various other sources. A latent fingerprint 104 is a fingerprint that cannot be recovered by the conventional method of dusting. While the latent fingerprint 104 is clearly illustrated here, it is understood that an actual latent fingerprint 104 may not be visible to the naked eye. The object 102 is placed 103 in a refrigerator 106, or cold chamber 106, and chilled to below a current dew point in humidified air chamber 110. The temperature of object 104 may be measured directly or the object 104 may simply be left for an amount of time that experience shows is adequate to chill the object 102.

Once chilled, the object 102 is moved 108 into humidified air chamber 110, or wet chamber 110. In a humid environment, humid ambient atmosphere may substitute for humidified air chamber 110. Once condensation on object 102 has occurred, object 102 is moved 122 into heat accelerated CE vacuum chamber 112 preferably onto insulating pad 140, to reduce temperature exchange with the surface of heat accelerated CE vacuum chamber 112. Heat accelerated CE vacuum chamber 112 may be releasably hermetically sealed by lid 114, which has a sealed conduit 128 for admitting electrical power cord 126 into heat accelerated CE vacuum chamber 112 to supply power to heater 130. Heater 130 heats, at a computer-controlled appropriate time, a receptacle 132 containing cyanoacrylate to create CE. Temperature sensor 134 is coupled to exemplary USB control board 150 via signal conduit 138 through sealed conduit 136, as shown. Electronically controllable power supply 124 provides power to the heater 130 under control of the exemplary USB control board 150, which control is exerted over signal conduit 154.

Exemplary USB control board 150 is one of various commercially available that plug into a USB port 158 of a PC or laptop 156 to enable software on the laptop 156 to control the operation of devices connected to the USB control board 150. USB cable 152 couples the USB control board 150 to the laptop 156. The USB control board 150 also receives pressure data from pressure sensor 144 inside the heat accelerated CE vacuum chamber 112 over signal conduit 146 that enters the heat accelerated CE vacuum chamber 112 via sealed conduit 142. The USB control board 150 controls the operation of vacuum pump 116 which pumps down the heat accelerated CE vacuum chamber 112 through vacuum piping 118 and expels the air out vent 120.

Any one or more of signal conduits 148, 146, 138, and 154 may, in various alternate embodiments, be wireless, optical, or electrical signal conduits. In a particular embodiment, USB control board 150 may be inside the heat accelerated CE vacuum chamber 112 with only the USB cable 152 penetrating the heat accelerated CE vacuum chamber 112 through a sealed conduit and control of power flowing to the heater 130 is exerted on the portion of power line 126 that is within the heat accelerated CE vacuum chamber 112. For example, a variable resistance in the power line 126 actuated by a solenoid that is controlled by USB control board 150 could be used to control power to the heater 103 from inside the heat accelerated CE vacuum chamber 112.

The apparatus 100 includes at least the heat accelerated CE vacuum chamber 112 and a means for chilling the object 102 before it is placed in the heat accelerated CE vacuum chamber 112. The apparatus 100 preferably also includes a means for supplying humidified air, such as humidified air chamber 110, and an insulating pad 140 within the heat accelerated CE vacuum chamber 112. The apparatus 100 most preferably further includes a computerized controller 160, exemplified herein as a USB control board 150 coupled to a laptop computer 156.

Those of skill in the art, enlightened by the present disclosure, will appreciate that the use of vacuum for drying the moisture off the object 102 and not entirely off the latent fingerprint 104 is exemplary of a drying influence, and will be aware of other drying influences that may be used, such as a supply of dry air or electromagnetic radiation that selectively heats water but not the sebaceous material of the latent fingerprint 104. Likewise, the condensation method of covering the object 102 and the latent fingerprint 104 with water is exemplary of methods for coating the object with a thin film of water, which may include dunking the object in water, misting, or spraying. The exemplary methods are preferred, due to their adaptability into an integrated system 300 (see below) requiring no operator intervention, the evenness and thinness of the water film, and the controllability of the vacuum drying, but the invention is not limited to the examples.

Figure 2:
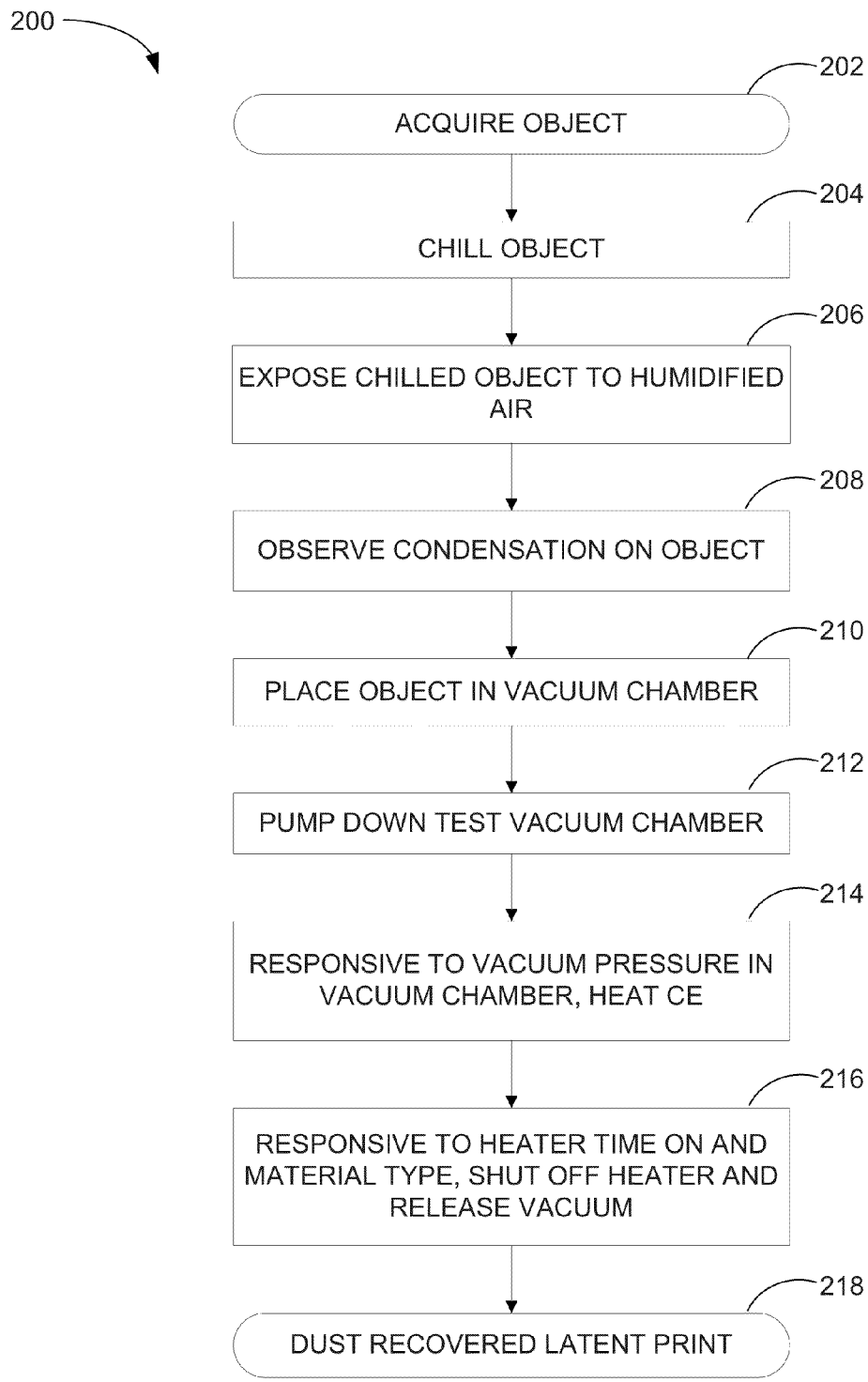
FIG. 2 is a process chart view illustrating an exemplary method for improved recovery of latent fingerprints on nonporous surfaces, according to a preferred embodiment of the present invention.

FIG. 2 is a process chart view illustrating an exemplary method 200 for improved recovery of latent fingerprints 104 on nonporous surfaces, according to a preferred embodiment of the present invention. In step 202, the object from which latent fingerprints 104 are to be recovered is acquired. In step 204, the object 104 is chilled below the dew point of an available source of humidified air, such as humidified air chamber 110. In step 206, the chilled object 104 is exposed to the source of humidified air 110. In step 208, the user observes the object 104 to verify that condensation has occurred. If not, steps 204 through 208 are repeated until condensation is observed. In a particular embodiment of step 208, the software may determine an appropriate time for observation, responsive to the type of material of the object 104, the humidity in the humidified air chamber 110, and the chill temperature of the object 104. Once condensation is observed in step 208, the object is, in step 210, placed in the heat accelerated CE vacuum chamber 112. Preferably, the object 102 is placed on an insulating pad 140 to avoid heat transfer to the heat accelerated CE vacuum chamber 112. As part of step 210, liquid cryanoacrylate is poured into the receptacle 132 and the lid 114 is closed and sealed. In step 212, the heat accelerated CE vacuum chamber 112 is pumped down toward vacuum. In step 214, responsive to the pressure sensed by pressure sensor 144, the software determines that the condensation has left the surface of object 102 but that at least some of the condensation still adheres to the sebaceous fluids of the latent fingerprint 104. At this point, the heater 130 is turned on to create heat-accelerated CE. The heat-accelerated CE adheres to the condensation-hydrated latent fingerprint 104, thereby recovering the latent fingerprint 104. In step 216, the heater is shut off and the vacuum is released under control, all responsive to the time the heater was on in light of the type of material making up the non-porous portion of the object 104. The result is a recovered latent fingerprint 104, which may be dusted in step 218. In a particular embodiment, the recovered latent print may be stained and/or optically scanned.

Figure 3:
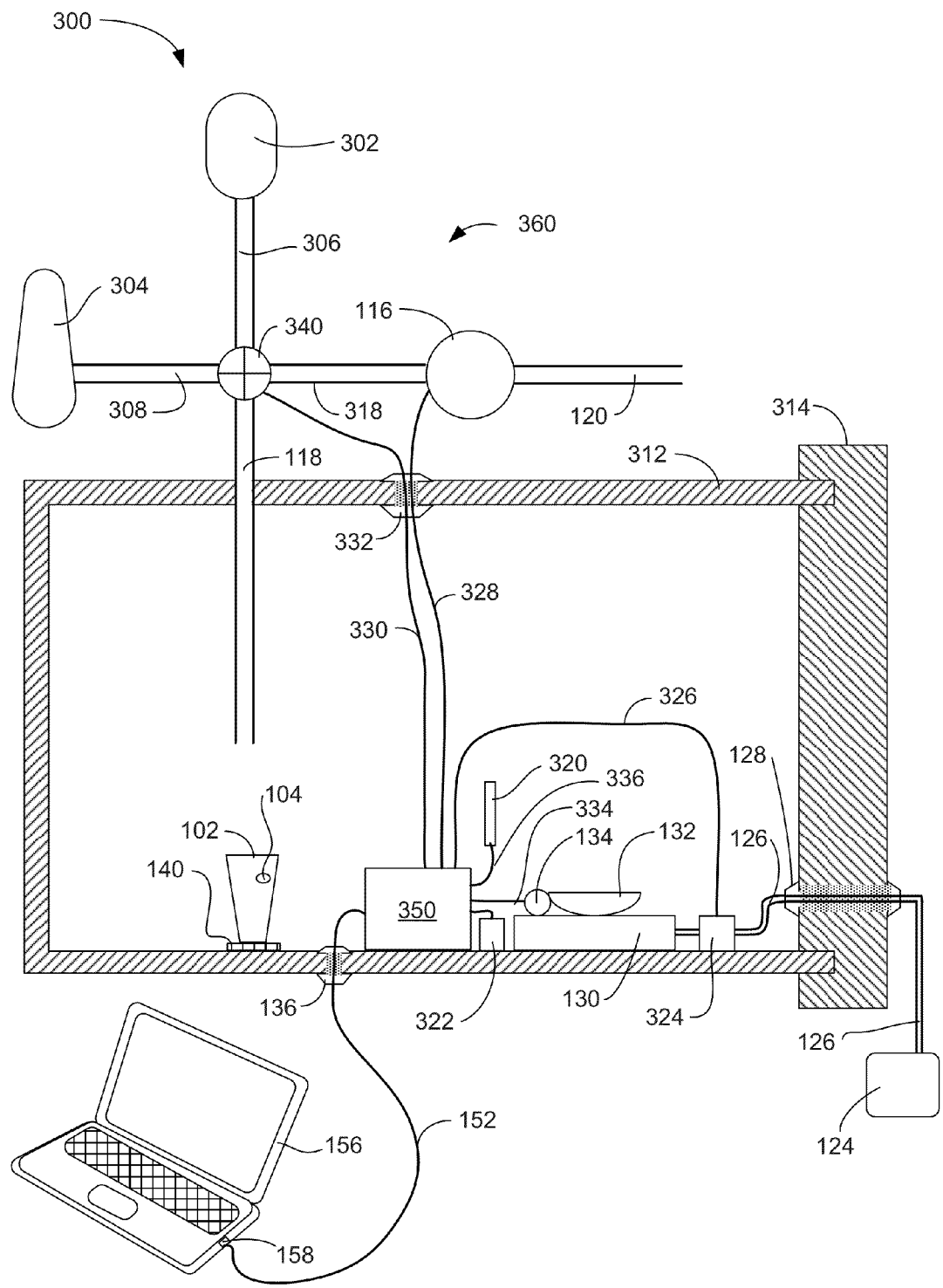
FIG. 3 is a diagram illustrating another exemplary apparatus for improved recovery of latent fingerprints on nonporous surfaces, according to another preferred embodiment of the present invention.

FIG. 3 is a diagram illustrating another exemplary apparatus 300 for improved recovery of latent fingerprints 104 on nonporous surfaces, according to another preferred embodiment of the present invention. Single chamber 312 is releasably hermetically sealed by lid 314. USE control board 350 is preferably located inside the chamber 312 and is coupled to external laptop 156 via a USB cable 152 that enters the chamber 312 through sealed conduit 136, as shown. The power supply 124, power cord 126, and power cord sealed conduit 128 are the same as for embodiment 100. Power to the heater 130 is controlled with actuator 324 that is controlled by USE control board 350 via signal conduit 326, where the USE control board 350 is under the direction of software on, and user inputs to, laptop 156. In various alternate embodiments, laptop 156 may be a PC, other computer, or logic having a USB port 158.

Heater 130 heats CE in receptacle 132 when actuator 324 supplies power to heater 130. Actuator 324 may be a solenoid-activated variable resistance, an off-on switch, or the like. In an alternate embodiment, receptacle 132 may be integral with heater 130. The temperature of the receptacle 132 is sensed by the thermal sensor 134 which is coupled to USB control board 350 via signal conduit 334. In alternate embodiments, thermal sensor 134 may be integral to the receptacle 132, the heater 130, or both.

Pressure sensor 322 senses the pressure within the chamber 312 and supplies pressure data to the USB control board 350 via a signal conduit (not labeled), as shown. Chamber ambient temperature sensor 320 senses the temperature in the chamber 312 and is used particularly during an atmospheric phase of operation of chamber 312 and supplies data to USB control board 350 via signal conduit 336. In alternate embodiments, one or both of the pressure sensor 322 and the chamber ambient temperature sensor 320 may be resident on the USB control board 350.

Exterior plumbing 360 includes a vacuum pump 116, a chilled gas source 302, a humidified air source 304, an electronically controllable valve 340, chamber gas control tube 118, vent 120, and valve-connective piping 306, 308, and 318. Electronically controllable valve 340 is communicatively coupled to USB control board 350 via signal conduit 330 through sealed conduit 332. The position of the electronically controllable valve 340 can be changed in response to signals from USB control board 350 to select either vacuum, chilled gas, or humidified air via chamber gas control tube 118. Vacuum pump 116 is controlled by signals from USB control board 350 via signal conduit 328. In alternate embodiments, any two or three of vacuum pump 116, chilled gas source 302, and humidified air source 304 may each be independently equipped with electronically controllable valves 340 and chamber gas control tubes 118 into chamber 312.

In operation, an object 102 that has at least some non-porous surface area upon which a latent fingerprint 104 is believed to exist is placed in the chamber 312 and the lid 314 is hermetically sealed to the chamber 312. Electronically controllable valve 340 is controlled to conduct chilled gas, such as liquefied air, liquid Nitrogen, refrigerated air, or the like from chilled gas source 302 through valve-connective pipe 306, electronically controllable valve 340, and chamber gas control tube 118 into the chamber 312 to chill object 102. Chamber ambient temperature is sensed by chamber ambient temperature sensor 320 and that temperature, along with a period of time that depends upon the material properties of object 102 (mass, thermal conductivity, etc.,) is used to time the chill-down period to bring the object to a temperature well below the dew point of the humidified air that is to be introduced after the chill-down period. In a particular embodiment, a sensor for sensing the temperature of the object 102 may be used. Additional sensors of various types, mentioned here and hereafter, add to the cost of the sys 300, and where other approaches to control are available, minimizing the number of sensors needed is preferred. However, as more experience is gained with the present invention, the present inventor recognizes that recovery of particularly difficult classes of latent fingerprints 104 may require finer control than timers can provide. In such difficult cases, additional sensors and refined control algorithms may be used.

Once the object 102 is chilled, a small amount of air is evacuated by vacuum pump 116 and then replaced with a predetermined amount of humidified air from humidified air source 304 by changing the state of valve 340. Humidified air source 304 may be a source of water or water vapor for introduction into the atmosphere within the chamber 312, or may be literally a source 304 of humidified air, humid climates, the source 304 of humidified air may be the natural ambient atmosphere. In another embodiment, the crime lab or other room in which the chamber 312 is operated may be kept at a sufficiently high humidity such that the ambient room air may be used as a source 304 of humidified air, a particular embodiment, an additional sensor for measuring condensation on the object 102 may be used to sense condensation on the surface of the object 102 and signal the USB control board 350 that condensation has occurred. For example, a sensor for sensing the reflectivity of the surface of the object 102, or a sensor for sensing the electrical conductivity of the surface of the object 102 may be used. In a particular embodiment, a humidity sensor may be used within the chamber 312 to report the chamber humidity to the USB control board 350 for use by software in laptop 156.

Whether condensation is sensed directly or inferred from chill-down temperature, humidity added to the chamber 312, and time, the system will change stage after condensation is determined to have occurred. After condensation, valve 340 again changes state in response to signals from USB control board 350, as controlled by software on laptop 156, to pump down the chamber 312 to about twenty-seven inches (mercury) of vacuum. As the chamber 312 is pumped down, the pressure in the chamber 312 is monitored using pressure sensor 322. When the chamber 312 pressure reaches a level that indicates that the condensation has just left the surface of the object 104, the heater 130 is turned on to accelerate vaporization of the cyanoacrylate into CE. In a particular embodiment, the point at which the condensation has just left the surface of the object may be directly sensed by a condensation sensor, as described above. After a predetermined time, the adhesion of the heat-accelerated CE to the latent fingerprint 104 is deemed to have occurred, and the vacuum in chamber 312 is released through vacuum pump 116 or through a dedicated valve (not shown), and the lid 314 is opened and the object 102 with the recovered latent fingerprint 104 is removed.

In a particular embodiment, a video camera and light source may be placed within chamber 312 to observe the effectiveness of the recovery of latent fingerprint 104, and the software in laptop 156 may provide for repeating the process before pumping down the chamber 312 and opening lid 314 in cases where repetition is called for.

Figure 4:
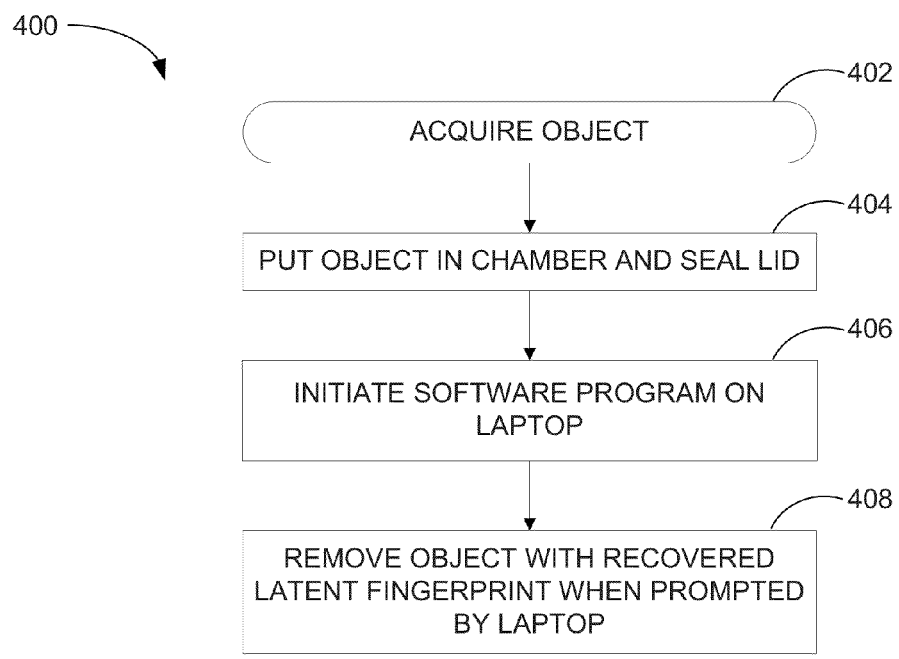
FIG. 4 is a process chart view illustrating another exemplar method for improved recovery of latent fingerprints nonporous surfaces, according to another preferred embodiment of the present invention.

FIG. 4 is a process chart view illustrating another exemplary method 400 for improved recovery of latent fingerprints 104 on nonporous surfaces, according to another preferred embodiment of the present invention. The object is acquired in step 402 and sealed into chamber 312 in step 404. The user initiates a software program on the laptop 156 in step 406, which automatically controls the process to completion. In step 408, the user removes the object 102 with the recovered latent fingerprint 104. The purpose of apparatus 300 and process 400 is to provide the user with a single unit, in which the user simply places an object 102 suspected of having latent fingerprints 104 into the chamber 312, and all operations take place in a single chamber 312 under computerized 156 control.

The control approaches disclosed herein are merely exemplary. Those of ordinary skill in the art, enlightened by the present disclosure, will be aware of the various choices of sensors, actuators, and control approaches that may be used to accomplish the objective of a single chamber 312 that can receive an object 102, chill object 102, condense moisture onto object 102, remove the condensed moisture from the surface of the object but not from the latent fingerprint 104 using a vacuum, and recover the condensation-hydrated latent fingerprint 104 using heat-accelerated CE. Condensation is the preferred method for wetting the surface of object 102 because it wets the entire surface evenly and can be done inside the chamber 312 without moving liquid water. In embodiments alternate to embodiment 100, other methods of waling the surface may be used, such as misting or submerging.

Determination of the point at which the vacuum has removed the condensation from the surface of the object 102 but has not yet removed the condensation from the sebaceous fluids that make up the latent fingerprint 104, is critical. The present inventor has discovered that, for glass, the time to start heat-accelerated CE is five minutes after reaching twenty-seven inches of vacuum, using his original prototype device. As more experience is gained in the use of this new system 100, 300, a database of heat-accelerated CE start times can be developed for various materials that might make up an object 102. The laptop 156 can then be programmed to respond to user input of the particular material type by selecting the corresponding heat-accelerated CE start time for that particular material.

Although applicant has described applicant's preferred embodiments of this invention, it will be understood that the broadest scope of this invention includes such modifications as diverse shapes and sizes and materials. Such scope is limited only by the below claims as read in connection with the above specification. Further, many other advantages of applicant's invention will be apparent to those skilled in the art from the above descriptions and the below claims.

I claim:

1. An apparatus for recovering a latent fingerprint that is on an object, the apparatus comprising:
   a. a cooler operable to initially chill such object;
   b. a humidifier subsequently operable to condense a thin uniform coating of water over all exposed surfaces of such chilled object bearing such latent fingerprint and over such latent fingerprint; and
   c. a vacuum chamber subsequently operable to expose such object bearing such latent fingerprint to a vacuum for a period of time automatically controlled to be sufficient to remove said thin uniform coating of water from such object and not entirely remove such water from such latent fingerprint.

2. The apparatus of claim 1, wherein:
   a. said cooler comprises one of a refrigerator and a cold chamber operable to chill such object bearing such latent fingerprint to a temperature below the dew point of a particular supply of humidified air; and
   b. said humidifier comprises a supply of humidified air for exposing such object bearing such latent fingerprint to humidified air from said particular supply of humidified air for a period of time sufficient to condense water from said humidified air onto said all exposed surfaces of such object bearing such latent fingerprint and onto such latent fingerprint.

3. The apparatus of claim 2, wherein said cold chamber is operable to contain one of a cold gas and a combination of cold gases.

4. The apparatus of claim 2, wherein said humidifier comprises a wet chamber configured to contain humidified air.

5. The apparatus of claim 2, wherein said vacuum chamber comprises a heat accelerated cyanoacrylate ester vacuum chamber.

6. The apparatus of claim 2, wherein said cold chamber, a wet chamber, and a heat accelerated cyanoacrylate ester vacuum chamber comprise a single chamber.

7. The apparatus of claim 1, further comprising said vacuum chamber operable to expose such condensation-hydrated latent fingerprint to cyanoacrylate ester for a period of time automatically controlled to be sufficient to coat such condensation-hydrated latent fingerprint with said cyanoacrylate ester.

8. The apparatus of claim 7, wherein said vacuum chamber for exposing such condensation-hydrated latent fingerprint to cyanoacrylate ester comprises a heat accelerated cyanoacrylate ester vacuum chamber.

9. The apparatus of claim 8, wherein said heat accelerated cyanoacrylate ester vacuum chamber further comprises an insulating pad adjacent to such object and adjacent to an interior surface of said heat accelerated cyanoacrylate ester vacuum chamber.

10. The apparatus of claim 1, further comprising a single hermetically resealable heat accelerated cyanoacrylate ester vacuum chamber for receiving such object bearing such latent fingerprint, wherein said single hermetically resealable heat accelerated cyanoacrylate ester vacuum chamber includes:
   a. humidification and cooling sufficient to create a thin uniform coating of water over said all exposed surfaces of such object bearing such latent fingerprint, wherein said humidification and cooling comprises:
      i. a supply of one of a cold gas and cold gases for chilling such object bearing such latent fingerprint to a temperature below the dew point of a supply of humidified air; and
      ii. valves and pipe between a supply of humidified air and said single hermetically resealable heat accelerated cyanoacrylate ester vacuum chamber operable to expose such object bearing such latent fingerprint to humidified air from said supply of humidified air for a period of time automatically controlled to be sufficient to condense water from said humidified air onto such object bearing such latent fingerprint;
   b. a vacuum pump fluidically coupled to said chamber and operable to expose such object bearing such condensation-hydrated latent fingerprint to a vacuum for a period of time automatically controlled to be sufficient to remove said thin uniform coating of water from such object and not entirely remove such water from such condensation-hydrated latent fingerprint.

11. The apparatus of claim 10, wherein said single hermetically resealable heat accelerated Cyanoacrylate Ester vacuum chamber further comprises a cyanoacrylate vaporizer operable to expose such condensation-hydrated fingerprint to cyanoacrylate ester for a period of time automatically controlled to be sufficient to coat such condensation-hydrated fingerprint with said cyanoacrylate ester.

12. The apparatus of claim 11, further comprising a controller coupled to said single hermetically resealable heat accelerated cyanoacrylate ester vacuum chamber and operable to control said supply of one of a cold gas and cold gases, said supply of humidified air, said vacuum supply, and said cyanoacrylate ester vaporization, all in timing relationships that enable recovering such latent fingerprint without operator intervention.

13. The apparatus of claim 12, wherein said controller comprises a USB control board communicatively coupled to a computer, wherein said computer comprises control software for said apparatus.

14. The apparatus of claim 12, further comprising at least one computer-controllable valve for controlling one of a cold gas supply, a vacuum source, and a humidified air supply.

15. The apparatus of claim 12, further comprising at least one computer-readable sensor to sense at least one of chamber temperature, a chamber pressure, cyanoacrylate ester heater temperature, an object temperature, a condensation state, a power ON/OFF state, and at least one valve state.

* * * * *